United States Patent
Ait Aissa et al.

(10) Patent No.: US 10,160,713 B2
(45) Date of Patent: Dec. 25, 2018

(54) DEHYDRATION OF ALPHA-SUBSTITUTED CARBOXYLIC ACIDS IN THE PRESENCE OF WATER AT HIGH PRESSURES

(71) Applicant: EVONIK ROEHM GmbH, Darmstadt (DE)

(72) Inventors: Belaid Ait Aissa, Darmstadt (DE); Steffen Krill, Muehltal (DE); Matthias Groemping, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 9 days.

(21) Appl. No.: 15/316,685

(22) PCT Filed: Jun. 24, 2015

(86) PCT No.: PCT/EP2015/064233
§ 371 (c)(1),
(2) Date: Dec. 6, 2016

(87) PCT Pub. No.: WO2016/001033
PCT Pub. Date: Jan. 7, 2016

(65) Prior Publication Data
US 2018/0118650 A1 May 3, 2018

(30) Foreign Application Priority Data
Jul. 4, 2014 (DE) .................. 10 2014 213 016

(51) Int. Cl.
*C07C 57/04* (2006.01)
*C07C 51/377* (2006.01)

(52) U.S. Cl.
CPC .......... *C07C 51/377* (2013.01); *C07C 57/04* (2013.01); *Y02P 20/582* (2015.11)

(58) Field of Classification Search
CPC .............................. C07C 51/377; C07C 57/04
See application file for complete search history.

(56) References Cited

FOREIGN PATENT DOCUMENTS

| CA | 2688292 | * | 12/2008 |
|---|---|---|---|
| CN | 1938255 | | 3/2007 |
| CN | 102781899 | | 11/2012 |
| WO | 2008/145737 A1 | | 12/2008 |
| WO | 2013/137277 A1 | | 9/2013 |

OTHER PUBLICATIONS

Aida et al., "Dehydration of lactic acid to acrylic acid in high temperature water at high pressures," Journal of Supercritical Fluids, vol. 50, Issue 3, 2009, pp. 257-264.*
International Search Report dated Sep. 21, 2015 in PCT/EP2015/064233 filed Jun. 24, 2015.

* cited by examiner

*Primary Examiner* — Pancham Bakshi
*Assistant Examiner* — Mark R Luderer
(74) *Attorney, Agent, or Firm* — Grüneberg and Myers PLLC

(57) ABSTRACT

The present invention describes a process for dehydrating alpha-substituted carboxylic acids in the presence of water at high pressures while avoiding by-products.

16 Claims, 1 Drawing Sheet

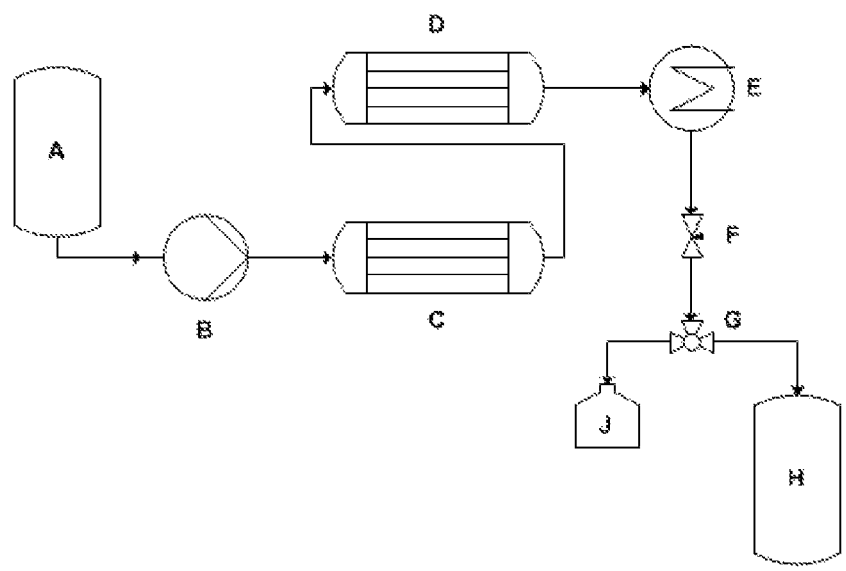

DEHYDRATION OF ALPHA-SUBSTITUTED CARBOXYLIC ACIDS IN THE PRESENCE OF WATER AT HIGH PRESSURES

The present invention describes a process for dehydrating alpha-substituted carboxylic acids (ASCA), particularly alpha-hydroxyisobutyric acid (HIBA), in the presence of water at high pressures while avoiding by-products.

Corresponding dehydration processes are disclosed in the prior art. CH 430691 describes the liquid-phase dehydration of HIBA dissolved in methanol using NaOH as catalyst to form methyl methacrylate (MMA) and methacrylic acid (MAA). The catalyst is added only in small amounts. Phthalic anhydride and tetraethylene glycol dimethyl ether are used as heat-transfer fluid to achieve the high temperature of 260° C.

Catalysts disclosed in DE 1768253 are alkali metal and alkaline earth metal salts of HIBA (Na, K, Li, Ca, Mg, Ba, Sr) employed in the form of hydroxides, carbonates, sulphites, acetates or phosphates for example. One preferred implementation of the dehydration is carried out at atmospheric pressure and 210-225° C. with addition of polymerization inhibitors. This disclosure also describes continuous addition of the catalyst and partial discharge of the reactor contents to avoid accumulation therein of catalyst and by-products. However, recovery of the target product thus necessarily likewise discharged is not described.

EP 487853 discloses a process for preparing methacrylic acid (MAA) comprising the steps of: a) Preparing acetone cyanohydrin (ACH) from acetone and HCN, b) obtaining hydroxyisobutyramide (HIBAm)—synthesis by ACH hydrolysis over $MnO_2$, c) homogeneously catalytic reaction of HIBAm with methyl formate or MeOH/CO to afford methyl hydroxyisobutyrate (MHIB) with formation of formamide and d) hydrolysis of MHIB to afford HIBA and subsequent dehydration to afford MAA. The final reaction step is described as continuous with addition of stabilizers. The difficulties thus inevitably encountered during long-term operation, due to accumulation of by-products etc., are not addressed in this document.

DE 1191367 discloses carrying out the dehydration of alpha-hydroxycarboxylic acids in the presence of Cu and hydroquinone as polymerization inhibitor and a mixture of alkali metal chlorides or bromides and corresponding halide salts of Zn, Sn, Fe, Pb as catalyst at temperatures of 185-195° C. Continuous operation and any potential problems with recycling are not described. In-house experiments show that the use of halide salts as catalyst also generates alpha-halogenated reaction by-products which need to be removed from the actual target product again by a correspondingly laborious procedure and that the use of halogenated compounds, due to their corrosiveness, necessitates the use of correspondingly durable industrial materials of construction, thereby making the process more costly overall.

DE 102005023975 describes carrying out the dehydration in the presence of at least one metal salt, for example alkali metal and/or alkaline earth metal salts, at temperatures of 160-300° C., particularly preferably 200-240° C. Metal salts described as suitable therein include, inter alia, sodium hydroxide, potassium hydroxide, calcium hydroxide, barium hydroxide, magnesium hydroxide, sodium sulphite, sodium carbonate, potassium carbonate, strontium carbonate, magnesium carbonate, sodium bicarbonate, sodium acetate, potassium acetate and sodium dihydrogenphosphate. A special feature is that the dehydration step and an upstream transesterification step are carried out at the same pressure preferably in the range of 0.1-1 bar. Discharging of by-products is not disclosed.

DE 2144304 describes the dehydration of alpha-hydroxycarboxylic acids and the simultaneous esterification thereof in the presence of alcohols using phosphates and/or sulphates as catalysts at water concentrations of up to 200 wt % based on the reactant acid.

SU 891631 proposes an improved process for preparing methacrylic acid from HIBA by elimination of water in the liquid phase, wherein the reaction is carried out in an autoclave at temperatures of 200-240° C. in the absence of a catalyst using an aqueous solution of HIBA comprising no more than 62 wt % of HIBA in water. Disadvantages of this process include not only the batchwise mode of operation but also long residence times.

Common to these prior art processes is, inter alia, that the conversions per pass are low which makes laborious separation of the product mixtures and recycling of the reactants necessary. This requires large amounts of energy, primarily steam and cooling energy. The catalytic mode of operation in the liquid phase in the presence of alkali metal-containing catalysts moreover leads to not inconsiderable formation of by-products, particularly dimeric or oligomeric forms of ASCA, which are formed from MAA by thermal ene reaction and consecutive decarboxylation for example. These by-products account for up to 10% of by-product formation depending on the reaction regime and even a reaction regime optimal in process engineering terms forms up to 3% of these by-products. To prevent accumulation of these by-products, it is generally necessary to discharge product streams at least to some extent and this is associated with undesired catalyst losses.

It is an object of the present invention to overcome the cited disadvantages of the prior art either completely or at least to a significant extent and to provide a process achieving high single pass conversions while at the same time making it possible to achieve selectivities >96% based on the target products. It is a further object to provide a catalyst-free process which avoids commercial disadvantages associated with the discharging and/or regenerating of same.

These objects and further objects not explicitly mentioned are achieved by the provision of a process for dehydrating alpha-substituted carboxylic acids, particularly alpha-hydroxyisobutyric acid, characterized in that the reaction is carried out in the presence of water and at pressures of 40-1000 bar.

It has now been found that, surprisingly, the process according to the invention achieves high conversions. The prior art, particularly the publication "Dehydration of lactic acid to acrylic acid in high temperature water at high pressures" (J. of Supercritical Fluids 50 (2009), 257-264), deters those skilled in the art from carrying out a dehydration of ASCA at high pressures in the presence of water since only very low conversions are to be expected. The similarity in reactivity typically ascribed to acrylic acid and MAA does not apply here. The process according to the invention achieves conversions of up to 90% in the dehydration of, in particular, HIBA to MAA which would not have been expected from the prior art.

It has moreover been found that there is a marked reduction in the formation of by-products in the process according to the invention. The formation of the abovementioned dimeric and oligomeric by-products in particular is minimized. The formation of said by-products accounts for a yield loss of up to 3% in the existing processes since they are difficult to remove from the product mixture. In accordance with the invention, the proportion of these dimers and oligomers in the crude MAA obtained downstream of the pressure reactor is less than 2%, preferably less than 1% and more preferably no more than 0.5%.

Reactants suitable for use in this process are alpha-substituted carboxylic acids of formula (1):

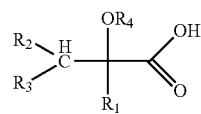
(1)

where $R_1$ is H or CHR'R"; $R_2$ and $R_3$ are each independently H or a carbon radical comprising 1-7 carbon atoms, linear, branched or alicyclic; $R_4$ is H or a carbon radical comprising 1-3 carbon atoms, linear or branched; R' and R" are each independently H or a carbon radical comprising 1-3 carbon atoms.

By-product typical of the dehydration reaction are, for example, dimeric or oligomeric forms of ASCA, open-chain or as cyclic compounds, and decarboxylation products formed from two dimeric ASCA units, primarily pentenoic acids (formula (2)) or hexenoic acids (formula (3)):

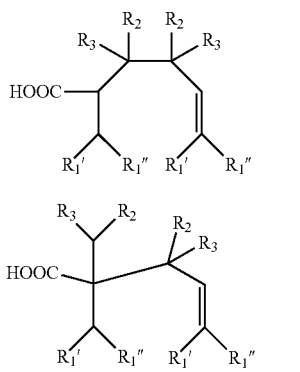
(2)
(3)

where all R substituents are each independently H or carbon chains comprising 1-3 carbon atoms. The former can be cleaved to reform the starting materials using a suitable process regime while the latter need to be discharged from the process permanently. These impurities are practically avoided in the process according to the invention, i.e., the concentration thereof is reduced to below the limit of detection.

The process according to the invention may suitably be carried out in pressure reactors known from the prior art, preference being given to continuous processes in tubular reactors.

The reaction pressures are 40-1000 bar, preferably 80-500 bar, more preferable 100-350 bar.

The residence times in the reactor are 1-300 s, preferably 3-60 s, more preferably 5-35 s.

The reaction is carried out at temperatures of 280-400° C., preferably 300-380° C., more preferably 320-360° C.

The water present during the reaction may be supplied to the reactor directly or via the feed. The feed itself may be supplied to the reactor as a separate feed of HIBA and water or as a mixture thereof. In a preferred version of the process according to the invention, HIBA unconverted in the reaction may be recycled into the reactor in which case the reaction water formed—1 mol per mole of MAA produced—must be discharged beforehand.

The water concentration during the reaction is 10-90%, preferably 30-70%, more preferably 40-60%, based on HIBA.

The process according to the invention preferably eschews catalyst but alkali metal or alkaline earth metal salts may be added as pH buffers or moderators. Suitable salts are hydroxides, halides, carbonates, phosphates or sulphates, preference being given to hydroxides.

An illustrative embodiment of the process according to the invention is shown in FIG. 1.

The following examples are intended to elucidate the process according to the invention but are not intended to restrict it in any way.

LIST OF DESIGNATIONS

A: reactant reservoir vessel
B: pump
C: preheater
D: reactor
E: heat exchanger
F: pressure maintenance valve
G: three-way cock
H: product reservoir vessel
J: sampling vessel

EXAMPLES 1-5

Examples 1-5 are carried out in a plant according to FIG. 1. Water and HIBA are initially charged into reservoir vessel A in a molar ratio of 13.5:1. Preheater C (heating block with heating coil) is preheated to 220° C. and reactor D (construction identical to preheater) is heated up to the particular reaction temperature required. The pressure maintenance valve F is set to 100 bar. The reactant mixture is pumped through the preheater and reactor via pump B, cooled down to room temperature in the heat exchanger and passes via three-way cock G into the reservoir vessel H. Periodic sampling is carried out in J. The results at various reactor temperatures are reported in Table 1.

EXAMPLES 6-10

Examples 6-10 are carried out analogously to Examples 1-5, the only difference being that the pressure is increased from 100 to 220 bar in each case. The results at various temperatures are likewise reported in Table 1.

TABLE 1

Temperature and pressure dependence

| Example | $H_2O$/HIBA mol/mol | Residence time s | Pressure bar | Temperature ° C. | Conversion % | MAA selectivity % |
|---|---|---|---|---|---|---|
| 1 | 13.5 | 16.8 | 100 | 280 | 16.0 | 98.4 |
| 2 | 13.5 | 16.8 | 100 | 300 | 37.6 | 98.1 |
| 3 | 13.5 | 16.8 | 100 | 320 | 65.2 | 98.0 |
| 4 | 13.5 | 16.8 | 100 | 340 | 83.8 | 97.6 |
| 5 | 13.5 | 16.8 | 100 | 360 | 92.0 | 96.0 |
| 6 | 13.5 | 16.8 | 220 | 280 | 16.0 | 98.3 |
| 7 | 13.5 | 16.8 | 220 | 300 | 37.6 | 98.3 |
| 8 | 13.5 | 16.8 | 220 | 320 | 65.2 | 98.2 |

TABLE 1-continued

Temperature and pressure dependence

| Example | $H_2O$/ HIBA mol/mol | Residence time s | Pressure bar | Temperature °C. | Conversion % | MAA selectivity % |
|---|---|---|---|---|---|---|
| 9 | 13.5 | 16.8 | 220 | 340 | 83.8 | 97.8 |
| 10 | 13.5 | 16.8 | 220 | 360 | 92.0 | 97.5 |

As is apparent from the data in Table 1, conversion increases significantly with increasing temperature while relatively high pressure tends to achieve improved selectivities for MAA.

EXAMPLES 11-22

Examples 11-22 are carried out analogously to Examples 1-5 at a constant 320° C. but with different water concentrations in the feed and various reactor residence times. The results for two different pressures are reported in Table 2.

TABLE 2

Water content

| Example | $H_2O$/ HIBA mol/mol | Residence time s | Pressure bar | Temperature °C. | Conversion % | MAA selectivity % |
|---|---|---|---|---|---|---|
| 11 | 52.0 | 10.0 | 100 | 320 | 68.1 | 99.8 |
| 12 | 13.5 | 10.0 | 100 | 320 | 56.5 | 97.3 |
| 13 | 3.9 | 10.0 | 100 | 320 | 49.0 | 89.2 |
| 14 | 52.0 | 20.0 | 100 | 320 | 86.4 | 99.1 |
| 15 | 13.5 | 20.0 | 100 | 320 | 77.2 | 94.8 |
| 16 | 3.9 | 20.0 | 100 | 320 | 72.3 | 91.8 |
| 17 | 52.0 | 10.0 | 220 | 320 | 70.4 | 99.5 |
| 18 | 13.5 | 10.0 | 220 | 320 | 66.5 | 94.3 |
| 19 | 3.9 | 10.0 | 220 | 320 | 60.2 | 92.1 |
| 20 | 52.0 | 20.0 | 220 | 320 | 86.8 | 99.5 |
| 21 | 13.5 | 20.0 | 220 | 320 | 85.8 | 93.9 |
| 22 | 3.9 | 20.0 | 220 | 320 | 76.8 | 89.8 |

As is apparent from the data in Table 2, relatively low water contents achieve poorer conversions and selectivities. When the reaction of HIBA is carried out without addition of water (no data shown), polymerization deposits in the reactor area and decomposition of HIBA are observed.

EXAMPLES 23-30

Examples 23-30 are likewise carried out analogously to Examples 1-5 but with different residence times. The results for two different temperatures are reported in Table 3.

TABLE 3

Residence times

| Example | $H_2O$/ HIBA mol/mol | Residence time s | Pressure bar | Temperature °C. | Conversion % | MAA selectivity % |
|---|---|---|---|---|---|---|
| 23 | 13.5 | 31.2 | 220 | 340 | 91.8 | 90.5 |
| 24 | 13.5 | 15.6 | 220 | 340 | 82.9 | 95.8 |
| 25 | 13.5 | 12.5 | 220 | 340 | 77.4 | 97.5 |
| 26 | 13.5 | 10.4 | 220 | 340 | 71.9 | 98.1 |
| 27 | 13.5 | 31.2 | 220 | 320 | 82.1 | 90.1 |
| 28 | 13.5 | 15.6 | 220 | 320 | 65.2 | 98.2 |
| 29 | 13.5 | 12.5 | 220 | 320 | 56.1 | 95.5 |
| 30 | 13.5 | 10.4 | 220 | 320 | 49.2 | 97.1 |

As is apparent from the data in Table 3, relatively short residence times achieve relatively high selectivities but with significantly reduced conversions.

EXAMPLES 31-33 AND COMPARATIVE EXAMPLES 1-3

Examples 31-33 and Comparative Examples 1-3 are likewise carried out analogously to Examples 1-5 but at a constant 320° C. and with different residence times. The results for the inventive pressure of 320 bar and the comparative pressure of 25 bar are reported in table 4.

TABLE 4

Comparative examples

| Comparative Example | $H_2O$/ HIBA mol/mol | Residence time s | Pressure bar | Temperature °C. | Conversion % | MAA selectivity % |
|---|---|---|---|---|---|---|
| 1 | 13.5 | 42.3 | 25 | 320 | 65.9 | 89.6 |
| 2 | 13.5 | 31.7 | 25 | 320 | 49.3 | 92.3 |
| 3 | 13.5 | 25.4 | 25 | 320 | 37.3 | 95.6 |
| 31 | 13.5 | 42.3 | 320 | 320 | 86.1 | 98.2 |
| 32 | 13.5 | 31.7 | 320 | 320 | 82.2 | 98.3 |
| 33 | 13.5 | 15.9 | 320 | 320 | 60.2 | 98.4 |

The inventive pressure of 320 bar achieves significantly higher conversions and selectivities as is apparent from the data in Table 4.

The invention claimed is:

1. Process for dehydrating alpha-substituted carboxylic acid of formula (1):

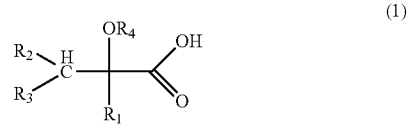

where $R_1$ is CHR'R"; $R_2$ and $R_3$ are each independently H or a carbon radical comprising 1-7 carbon atoms, linear, branched or alicyclic; $R_4$ is H or a carbon radical comprising 1-3 carbon atoms, linear or branched; R' and R" are each independently H or a carbon radical comprising 1-3 carbon atoms,
comprising reacting an alpha-substituted carboxylic acid of formula (1) in the presence of water and at pressures of 40-1000 bar.

2. Process according to claim 1, wherein said reaction is carried out at 280-400° C.

3. Process according to claim 1, wherein a residence time in a pressure reactor is 1-300 s.

4. Process according to claim 1, wherein the process is carried out as a catalyst-free process.

5. Process according to claim 1, wherein a crude methacrylic acid obtained downstream of a pressure reactor comprises less than 2% of dimeric or oligomeric by-products.

6. Process according to claim 1, wherein the process is carried out as a continuous process.

7. Process according to claim 1, wherein said alpha-substituted carboxylic acid is alpha-hydroxyisobutyric acid.

8. Process according to claim 1, wherein said pressure is 80-500 bar.

9. Process according to claim 1, wherein said pressure is 100-350 bar.

10. Process according to claim 3, wherein said residence time is 3-60 s.

11. Process according to claim 3, wherein said residence time is 5-35 s.

12. Process according to claim 2, wherein said temperature is 300 to 380° C.

13. Process according to claim 2, wherein said temperature is 320 to 360° C.

14. Process according to claim 1, wherein a concentration of water during reaction is 10-90% based on alpha-substituted carboxylic acid.

15. Process according to claim 1, wherein a concentration of water during reaction is 30-70% based on alpha-substituted carboxylic acid.

16. Process according to claim 1, wherein a concentration of water during reaction is 40-60% based on alpha-substituted carboxylic acid.

\* \* \* \* \*